US009867787B2

United States Patent
Lai et al.

(10) Patent No.: US 9,867,787 B2
(45) Date of Patent: Jan. 16, 2018

(54) HYPROMELLOSE-GRAFT-CHITOSAN AND METHODS THEREOF FOR SUSTAINED DRUG DELIVERY

(71) Applicant: THE UNIVERSITY OF HONG KONG, Hong Kong (CN)

(72) Inventors: Wing Fu Lai, Aberdeen (HK); Ho Cheung Shum, Kowloon (HK)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 15/130,368

(22) Filed: Apr. 15, 2016

(65) Prior Publication Data

US 2016/0310440 A1 Oct. 27, 2016

Related U.S. Application Data

(60) Provisional application No. 62/153,063, filed on Apr. 27, 2015.

(51) Int. Cl.
| | |
|---|---|
| *A61K 31/4164* | (2006.01) |
| *A61K 9/70* | (2006.01) |
| *A61K 31/65* | (2006.01) |
| *A61K 31/5415* | (2006.01) |
| *A61K 31/58* | (2006.01) |
| *A61K 47/38* | (2006.01) |
| *A61K 47/36* | (2006.01) |

(Continued)

(52) U.S. Cl.
CPC .......... *A61K 9/7007* (2013.01); *A61K 9/0019* (2013.01); *A61K 31/4164* (2013.01); *A61K 31/5415* (2013.01); *A61K 31/58* (2013.01); *A61K 31/65* (2013.01); *A61K 47/36* (2013.01); *A61K 47/38* (2013.01); *A61L 26/0023* (2013.01); *A61L 26/0066* (2013.01); *A61L 31/10* (2013.01); *A61L 31/16* (2013.01); *A61L 2300/20* (2013.01); *A61L 2300/606* (2013.01)

(58) Field of Classification Search
CPC ............ A61K 31/4164; A61K 31/5415; A61K 31/58; A61K 31/65; A61K 47/36; A61K 47/38; A61K 9/0019; A61K 9/7007; A61L 2300/20; A61L 2300/606; A61L 26/0023; A61L 26/0066; A61L 31/10; A61L 31/16
See application file for complete search history.

(56) References Cited

FOREIGN PATENT DOCUMENTS

| JP | 2010235537 A | 10/2010 |
|---|---|---|
| WO | WO2014197601 A1 | 12/2014 |

OTHER PUBLICATIONS

Nehar 2010 Masters Thesis 207 pages.*
(Continued)

*Primary Examiner* — Ernst V Arnold
(74) *Attorney, Agent, or Firm* — Leason Ellis LLP

(57) ABSTRACT

Described herein is a drug delivery system, which is based on a novel polymer namely hypromellose-graft-chitosan (HC), useful to deliver a drug to a patient in sustained and controlled release fashion. HC is highly water soluble across the pH range from 1.2 to 10, and has a high pH buffering capacity to provide a pH-stable environment for drug delivery. In addition, the drug delivery system provided herein exhibited a drug loading efficiency of over 90% in all drugs tested, which is 1-2 fold higher than the efficiency attainable by conventional chitosan, and achieved a 2-3 fold longer duration of sustained drug release.

22 Claims, 12 Drawing Sheets

(51) Int. Cl.
 A61K 9/00 (2006.01)
 A61L 26/00 (2006.01)
 A61L 31/10 (2006.01)
 A61L 31/16 (2006.01)

(56) References Cited

OTHER PUBLICATIONS

Rotta et al. (Ciênc. Tecnol. Aliment., Campinas, 2011;31(2): 450-455).*
Moller et al. (J. Agric. Food Chem. 2004;52:6585-6501).*
Bioconjugate reagents [online] retrieved on Jul. 29, 2017 from: https://www.researchgate.net/file.PostFileLoader.html?assetKey=AS%3A271752414859265%401441802232450&id=5020d0cbe39d5e7b54000034; pp. 213-233).*
Oh JE, Nam YS, Lee KH, Park TG. Conjugation of drug to poly(D,L-lactic-co-glycolic acid) for controlled release from biodegradable microspheres, Journal of Controlled Release. 1999;57:269-80.
Nam YS, Park JY, Han SH, Chang IS. Intracellular drug delivery using poly(D,L-lactide-co-glycolide) nanoparticles derivatized with a peptide from a transcriptional activator protein of HIV-1. Biotechnology Letters. 2002;24:2093-8.
Luo RC, Cao Y, Shi P, Chen CH. Near-infrared light responsive multi-compartmental hydrogel particles synthesized through droplets assembly induced by superhydrophobic surface. Small. 2014;10:4886-94.
Kearns VR, Williams RL. Drug delivery systems for the eye. Expert Review of Medical Devices. 2009;6:277-90.
Chu LY, Yamaguchi T, Nakao S. A molecular-recognition microcapsule for environmental stimuli-responsive controlled release. Advanced Materials. 2002;14:386-9.
Kim SH, Kim JW, Kim DH, Han SH, Weitz DA. Polymersomes containing a hydrogel network for high stability and controlled release. Small. 2013;9:124-31.
Kolhe P, Misra E, Kannan RM, Kannan S, Lieh-Lai M. Drug complexation, in vitro release and cellular entry of dendrimers and hyperbranched polymers. International Journal of Pharmaceutics. 2003;259:143-60.
Feng XL, LV FT, Liu LB, Tang HW, Xing CF, Yang QO, et al. Conjugated polymer nanoparticles for drug delivery and imaging. ACS Applied Materials & Interfaces. 2010;2,.
Xu XD, Liang LA, Chen CS, Lu B, Wang NL, Jiang FG, et al. Peptide hydrogel as an intraocular drug delivery system for inhibition of postoperative scarring formation. ACS Applied Materials & Interfaces. 2010,;2:2663-71.
Manna U, Patil S. Glucose-triggered drug delivery from borate mediated layer-by-layer self-assembly. ACS Applied Materials & Interfaces. 2010;2:1521-7.
Fatouros DG, Lamprou DA, Urquhart AJ, Yannopoulos SN, Vizirianakis IS, Zhang SG, et al. Lipid-like self-assembling peptide nanovesicles for drug delivery. ACS Applied Materials & Interfaces. 2014;6:8184-9.
Zhao J, Lu C, He X, Zhang X, Zhang W, Zhang X. Polyethylenimine-grafted cellulose nanofibril aerogels as versatile vehicles for drug delivery. ACS Applied Materials & Interfaces. 2015;7:2607-15.

Lima HA, Lia FMV, Ramdayal S. Preparation and characterization of chitosan-insulin-tripolyphosphate membrane for controlled drug release: effect of cross linking agent. Journal of Biomaterials and Nanobiotechnology. 2014;5:211-9.
Li CL, Martini LG, Ford JL, Roberts M. The use of hypromellose in oral drug delivery. Journal of Pharmacy and Pharmacology. 2005;57:533-46.
Nunthanid J, Huanbutta K, Luangtana-Anan M, Sriamornsak P, Limmatvapirat S, Puttipipatkhachorn S. Development of time-, pH-, and enzyme-controlled colonic drug delivery using spray-dried chitosan acetate and hydroxypropyl methylcellulose. European Journal of Pharmaceutics and Biopharmaceutics. 2008;68:253-9.
Kim SK, Rajapakse N. Enzymatic production and biological activities of chitosan oligosaccharides (COS): A review. Carbohydrate Polymers. 2005;62:357-68.
Pal S, Nasim T, Patra A, Ghosh S, Panda AB. Microwave assisted synthesis of polyacrylamide grafted dextrin (Dxt-g-PAM): Development and application of a novel polymeric flocculant. International Journal of Biological Macromolecules. 2010;47:623-31.
Shahid M, Bukhari SA, Gul Y, Munir H, Anjum F, Zuber M, et al. Graft polymerization of guar gum with acryl amide irradiated by microwaves for colonic drug delivery. International Journal of Biological Macromolecules. 2013;62:172-9.
Lorenzo-Lamosa ML, Remunan-Lopez C, Vila-Jato JL, Alonso MJ. Design of microencapsulated chitosan microspheres for colonic drug delivery. Journal of Controlled Release. 1998;52:109-18.
Nakagawa K, Sowasod N, Tanthapanichakoon W, Charinpanitkul T. Hydrogel based oil encapsulation for controlled release of curcumin by using a ternary system of chitosan, kappa-carrageenan, and carboxymethylcellulose sodium salt. LWT-Food Science and Technology. 2013;54:600-5.
Lu SY, Liu MZ, Ni Bl. An injectable oxidized carboxymethylcellulose/N-succinyl-chitosan hydrogel system for protein delivery. Chemical Engineering Journal. 2010;160:779-87.
Gomez-Burgaz M, Garcia-Ochoa B, Torrado-Santiago S. Chitosan-carboxymethylcellulose interpolymer complexes for gastric-specific delivery of clarithromycin. International Journal of Pharmaceutics. 2008;359:13C5-43.
Yan LF, Qian F, Zhu QS. Interpolymer complex polyampholytic hydrogel of chitosan and carboxymethyl cellulose (CMC): synthesis and ion effect. Polymer International. 2001;50:1370-4.
Alencastre JB, Bentley MVLB, Garcia FS, de Moragas M, Viladot JL, Marchetti JM. A study of the characteristics and in vitro permeation properties of CMC/ chitosan microparticles as a skin delivery system for vitamin E. Revista Brasileira de Ciências Farmacêuticas. 2006;42:69-76.
Li P, Dai YN, Zhang JP, Wang AQ, Wei Q. Chitosan-alginate nanoparticles as a novel drug delivery system for nifedipine. International Journal of Biomedical Science. 2008;4:221-8.
Mellott MB, Searcy K, Pishko MV. Release of protein from highly cross-linked hydrogels of poly(ethylene glycol) diacrylate fabricated by UV polymerization. Biomaterials. 2001;22:929-41.
Lee JW, Kim SY, Kim SS, Lee YM, Lee KH, Kim SJ. Synthesis and characteristics of interpenetrating polymer network hydrogel composed of chitosan and poly(acrylic acid). Journal of Applied Polymer Science. 1999;73:113-20.
Lai and Shum. Hypromellose-graft-chitosan and its polyelectrolyte complex as novel systems for sustained drug delivery. ACS Appl Mater Interfaces. 2015: 7(19):10501-10.

* cited by examiner

A          B

HYPROMELLOSE-GRAFT-CHITOSAN AND METHODS THEREOF FOR SUSTAINED DRUG DELIVERY

CROSS-REFERENCE TO RELATED PATENT APPLICATIONS

This application claims priority to U.S. Provisional Application Ser. No. 62/153,063 filed on Apr. 27, 2015, which is incorporated by reference herein in its entirety.

1. INTRODUCTION

Disclosed herein is a novel polymer, hypromellose-graft-chitosan (HC), which is used in a system for sustained and controlled release delivery of a drug to a subject. In certain embodiments, the drug is a chemical, a small molecule or a biologics. Also disclosed herein is a process for making HC from chitosan which has improved aqueous solubility.

2. BACKGROUND

Conventional drug administration methods entail periodic dosing of a therapeutic agent in a formulation that ensures drug activity, stability and bioavailability. These methods include topical administration using salves or ointments for skin applications, parenteral administration by injection, and oral administration by ingestion (e.g. tables, pills, and liquids). These methods reduce drug bioavailability by various factors (particularly the physiological barriers and blood clearance), as drug administration typically leads to a sharp initial increase in drug concentration, followed by a steady decline in concentration as the drug is cleared and/or metabolized. Periodic dosing is required to reach and maintain the drug concentration within the appropriate efficacy range. The consequence of this repeated administration is a drug concentration profile that oscillates over time. Such oscillation and initial burst of drug release are particularly undesirable for drugs that are unstable in the blood stream or gastrointestinal tract, are toxic at high doses or have a narrow therapeutic window.

To resolve these difficulties, efforts have been directed over the last several decades to develop alternative drug carriers for more sustained drug action. Due to the ease of functionalization, low cost and the possibility of mass production, polymers are promising candidates for development of drug delivery systems. In this approach, the drug is dispersed within a polymeric matrix, which is wettable (i.e. capable of imbibing water) and serves to control the rate at which the drug is released. Polymeric delivery vehicles offer several advantages over conventional methods of drug administration, such as localization to the desired target site by implantation, topical application or by ingestion. This increases drug potency and reduces systemic toxicity. Polymeric delivery vehicles also release drugs at a controlled rate, thereby maintaining plasma drug concentration within an appropriate therapeutic window and reducing harmful side effects. Lastly, patient compliance is improved because the discomfort that accompanies periodic dosing is eliminated.

Among different polymers studied for polymeric delivery, chitosan (CS) is one polymer that has received significant interest because of its biocompatibility, biodegradability, non-allergenicity and non-toxicity. Chitosan is created via deacetylation reaction of chitin by treating crustacean animal shells with sodium hydroxide. For medical use, CS can be used to help deliver drugs through the skin.

However, current drug delivery applications of CS are highly limited because CS is insoluble in most solvents. CS is generally soluble in lower pH dilute organic acids, such as acetic acid, formic acid, succinic acid, lactic acid, and malic acid. This makes any CS drug delivery method highly pH-sensitive, and further limits CS application to pH-insensitive drugs. Further, current CS-based drug carriers have limited drug loading capacity and drug release sustainability.

As CS-based drug delivery systems have the benefits of biocompatibility, biodegradability, non-allergenicity and non-toxicity, but are limited by solubility and drug delivery capacities, thus, there exists a need in the art for CS-based drug delivery systems and methods that do not require acidic media for dissolution. There is also a need for CS-based drug delivery systems and methods that can load pH-sensitive drugs with high efficiency, increased drug loading capacity and drug release sustainability.

3. SUMMARY

An object of the present disclosure is to provide a polyelectrolyte complexes formed between chitosan (CS) and anionic polymers. In particular, CS-based copolymer when complexed with a polyelectrolyte, achieves more effective drug encapsulation and more sustained drug release than unmodified CS. It is an object of the present disclosure to provide a water-soluble, biocompatible and non-toxic copolymer in a pH-stable environment for drug delivery. Provided herein is a CS-based polymer, effective for drug encapsulation and sustained drug release. In one or more embodiments, the CS-based polymer comprises hypromellose-graft-CS (HC). In certain embodiments, HC is synthesized by copolymerizing CS with hypromellose via a coupling reagent-mediated approach. In one or more embodiments, the CS-based polymer is complexed with a polyelectrolyte. In one embodiment, the polyelectrolyte is carboxymethyl cellulose (CMC). In certain embodiments, the CS-based polymer is formulated with a second polymer to prepare a hydrogel. In some embodiments, the CS-based polymer has improved drug encapsulation efficiency and drug release sustainability as compared with unmodified CS.

Further provided herein is a drug delivery system and method for controlled and sustained delivery of therapeutic amounts of one or more drugs to a subject. In certain embodiments, the drug delivery system comprises a matrix which comprises one or more drugs dispersed therein. In certain embodiments, the system and method include a matrix formed of a wettable polymer and a multiplicity of drug particles dispersed uniformly within the polymer. In certain embodiments, the system and method includes a coupling reagent-mediated approach to copolymerize CS to hypromellose. In further embodiments, the drug delivery system and method includes chemicals such as tetracycline chloride (TH), methylene blue (MB), mometasone furoate (MF) and metronidazole (MT). In other embodiments, the drug delivery system and method include any other suitable chemicals. In certain embodiments, the drug delivery system and method deliver a drug-containing polymer via implantation, topical delivery, or ingestion. In specific embodiments, the drug is delivered via wound dressing, gel, foam, patch, film, bandage, tablet, pill, or paste. In certain embodiments, the drug is delivered locally. In certain embodiments, the drug is delivered topically. In certain embodiments, the drug is delivered systemically.

Also provided herein is a method of making HC by derivatizing conventional CS for improved aqueous solubility. In some embodiments, the method includes a controlled and sustained drug delivery system useful to deliver a drug to a patient. The system comprises delivery of substantially homogeneous particles. In certain embodiments, the substantially homogeneous particles are dispersed in a wettable polymeric matrix. Also disclosed is the method of preparing a polymeric matrix comprising HC.

Provided herein is a drug delivery system for controlled and sustained delivery of the drug to a patient comprising: a matrix comprising a hypromellose-graft-chitosan (HC) or a HC polyelectrolyte complex; and a drug dispersed in the matrix.

In one embodiment, provided herein is CS which is copolymerized with hypromellose via a coupling reagent-mediated approach to form a water-soluble, nontoxic CS derivative, namely hypromellose-graft-CS (HC), which is subsequently complexed with carboxymethylcellulose (CMC) to generate a polyampholytic hydrogel. When compared with conventional CS, HC is highly water-soluble across a wide pH range, and has a substantially higher pH buffering capacity to provide a pH-stable environment for delivery of drugs. In addition, the polyelectrolyte complex of HC exhibits a drug encapsulation efficiency of over 90% in all drugs tested, which is 1-2 fold higher than the efficiency attainable by the polyelectrolyte complex of conventional CS, with a 2-3 fold longer duration of sustained drug release.

Provided herein is a method for delivering drugs to a patient comprising the step of administering the drug delivery system disclosed herein.

Provided herein is a method of preparing a drug delivery system comprising the steps of: reacting chitosan with hypromellose to form a matrix comprising hypromellose-graft-chitosan (HC); and dispersing a drug in the matrix. In certain embodiment, the method further comprises reacting the HC with a polyelectrolyte to form a HC polyelectrolyte complex prior to dispersing the drug in the matrix.

Also disclosed is a polymer for drug delivery comprising a hypromellose-graft-chitosan (HC) wherein the HC is formed by reacting hypromellose with chitosan.

Also disclosed is a polymer for drug delivery comprising a HC polyelectrolyte complex which is formed by reacting a HC with a polyelectrolyte.

Also described herein is a composition comprising the HC as disclosed herein. In certain embodiments, the composition is a pharmaceutical composition that includes solutions, suspensions, gels, fluid gels, emulsions, emulsion gels, lotions, ointments, film forming solutions, creams and sprays. In particular, the composition is used to treat or prevent diseases in a subject. In specific embodiment, the subject is a mammal. In specific embodiment, the subject is human. In one embodiment, provided herein is a method of treating a disease comprising administering to a subject, a pharmaceutical composition comprising a therapeutically effective amount of HC comprising a drug. Also provided herein is a medical device comprising a coating comprising the delivery system as presented. In certain embodiments, the medical device is an implant. In one embodiment, the medical device is a stent. In certain embodiments, the medical device is a film. In certain embodiment, the film is absorbed over time after administration. Provided herein is a method of making a medical device comprising a coating comprising the delivery system disclosed herein.

Also disclosed is a kit comprising the drug delivery system provided herein. The kits comprise a carrier being compartmentalized to receive in close confinement one or more container such as vials, tubes, and the like, each of the container comprising one of the separate elements to be used in the method. The kit may include containers for other components, for example, buffers useful in the disclosed methods. The kit also contain instructions for mixing, diluting, and/or administrating the compounds. The kit also include other containers with one or more solvents, surfactants, preservative and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the drug and the mode of use or administration.

A kit as provided herein comprises a unit dose of a composition provided herein, or a second agent or composition, can include a dosage such that when administered to a subject, a therapeutically or prophylactically effective plasma level of the compound or composition can be maintained in the subject for at least 1, 2, 3, 4, 5, 6, 7 days. In some embodiments, a composition can be included as a sterile aqueous pharmaceutical composition or dry powder (e.g., lyophilized) composition. In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like.

These and other aspects, features, and advantages can be appreciated from the accompanying description of certain embodiments of the disclosure and the accompanying drawing figures and claims.

4. DESCRIPTION OF THE FIGURES

FIG. 1 shows the synthesis and putative chemical structure of hypromellose-graft-CS (HC).

FIGS. 2(A)-(D) show scanning electron microscope (SEM) micrographs at different magnification of (A) and (C) CS; and (B) and (D) HC.

FIGS. 3(A)-(F) show the structural characterization of HC according to: (A) $^1$H-NMR spectra of CS, (C) hypromellose and (E) HC; and FT-IR spectra of (B) CS, (D) hypromellose and (F) HC.

FIGS. 4(A) and (B) are graphical representations of: (A) the solubility of CS and HC at different pH values; and (B) the buffering capacity profiles of CS, hypromellose and HC.

FIGS. 5(A) and (B) show the method of preparation of the HC/CMC polyelectrolyte complex, specifically: (A) procedures for complex formation; and (B) a schematic diagram showing complexation of HC with CMC via electrostatic interactions for encapsulation of drug molecules.

FIGS. 6(A) and (B) are graphical representations of the cytotoxicity of CS, HC and CMC in rat retinal Müller rMC-1 cells after: (A) 5-hour incubation; and (B) 24-hour incubation.

FIGS. 7(A) and (B) are graphical representations of: (A) drug encapsulation efficiencies of HC/CMC and CS/CMC;

and (B) the effect of the molecular weight of drug molecules on the encapsulation efficiency of HC/CMC and CS/CMC.

Figure 10:
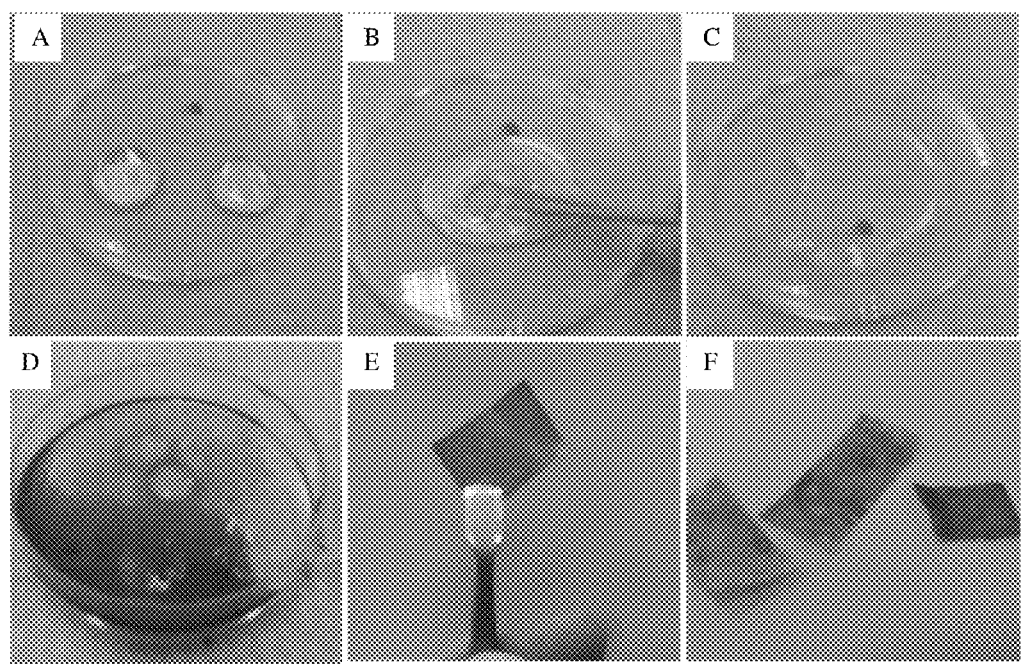

FIGS. 10 A-F illustrate the methods of making HC-based films for drug loading and delivery.

Figure 11:
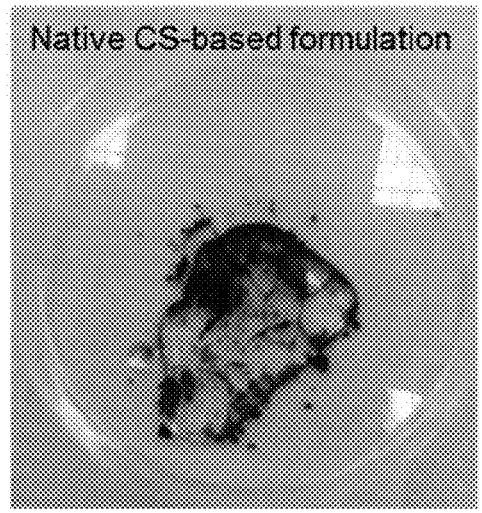
Figure 11:
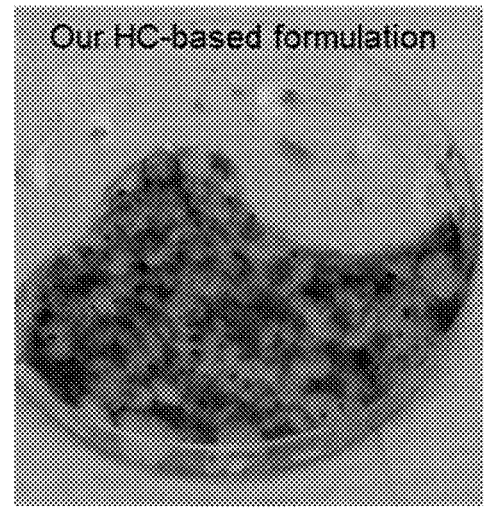

FIG. 11 A-B are comparison of (A) the HC-based formulation and (B) CS-based formulation in loading the hydrophobic drug modal. As shown in the figures, the molecules of the drug modal do not mix with the native CS-based formulation, leading to poor drug loading performance. On the contrary, the HC-based formulation disclosed herein allows for effective mixing and encapsulation of the hydrophobic drug modal.

Figure 12:
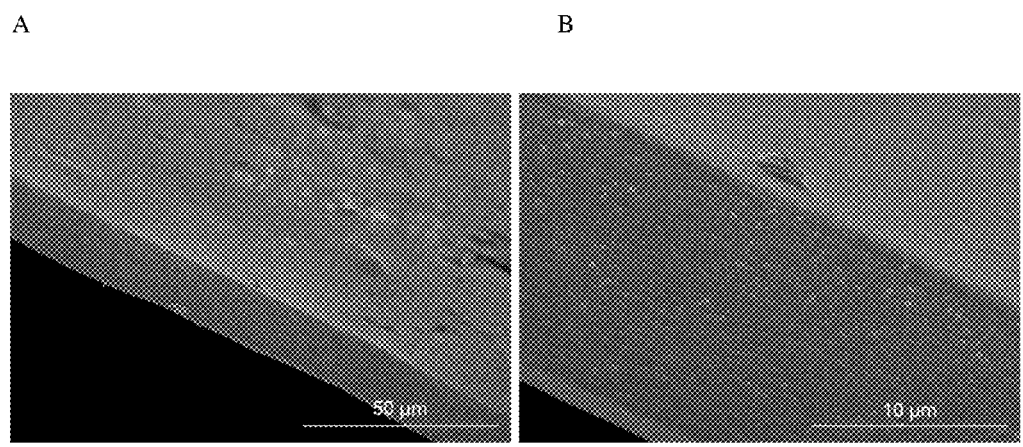

FIGS. 12 A-B are SEM micrographs of the HC-based drug loaded film. The drug molecules are shown to be effectively loaded into the film.

4.1 DEFINITION

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In another embodiment, the subject is a farm animal (e.g., a horse, a cow, a pig, etc.) or a pet (e.g., a dog or a cat). In one embodiment, the subject is a human.

As used herein, the terms "compound" and "agent" are interchangeable.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In one embodiment, a therapeutic agent is an agent which is known to be useful for, or has been or is currently being used for the treatment or prevention of a disorder or one or more symptoms thereof. "Therapeutically effective amount" includes an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a composition provided herein. In certain other embodiments, the term "prophylactic agent" does not refer a composition provided herein. For example, a prophylactic agent is an agent that is known to be useful for, or has been or is currently being used to prevent or impede the onset, development, and progression of disorder or symptoms.

5. DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter. It is to be understood that particular features, structures, or characteristics described may be combined in various ways in one or more implementations.

Chitosan (CS) is a biocompatible, slowly biodegradable and non-toxic biopolymer that are used as a carrier for controlled drug release. However, CS is hydrophobic, which together with CS's low drug encapsulation capacity, limits drug release sustainability. Moreover, the processing and wide pharmaceutical uses of CS require acidic media for dissolution and thereby fail to deliver pH-sensitive drugs.

The following examples illustrate the synthesis and use of representative embodiments provided herein. These examples are not intended, nor are they to be construed, as limiting the scope of the claimed subject matter. It will be clear that the scope of subject matter may be practiced otherwise than as particularly described herein. Numerous modifications and variations of the subject matter are possible in view of the teachings herein and, therefore, are within the scope the claimed subject matter.

In one embodiment, disclosed herein is a coupling reagent-mediated approach to copolymerize CS with hypromellose. Hypromellose (hydroxypropyl methylcellulose) is derived from cellulose and is soluble in water. In the present embodiment, hypromellose and CS are coupled to enhance aqueous solubility, buffering capacity, and/or EWC/swelling capacity. The coupling of hypromellose to CS was achieved by using 1,1'-carbonyldiimidazole (CDI), which activates the hydroxyl groups of hypromellose molecules to form active imidazolyl carbamate intermediates, which are then attacked by primary amine groups from CS, with imidazole being released as a by-product.

The drug delivery capacity of CS has been improved through polyelectrolyte complexation with oppositely charged polymers; however, the application of these complexes is still restricted by the properties of CS, including the low aqueous solubility and drug encapsulation capacity. The synthesis of hypromellose with CS to create hypromellose-graft-CS (HC) results in a polymer with higher aqueous solubility and the possibility for CS-drug delivery systems that do not require acidic dissolution media. Lai and Shum. Hypromellose-graft-chitosan and its polyelectrolyte complex as novel systems for sustained drug delivery. ACS Appl Mater Interfaces. 2015: 7(19):10501-10. The aqueous solubility of HC is between 1.5-5.0 fold higher than CS at different pH levels. HC can therefore be used to deliver drugs, including biologics, such as proteins, whose structure and bioactivity may be highly sensitive to the surrounding pH. Similarly, HC has a high pH buffering capacity, which provides a pH-stable environment for loading pH-sensitive drugs and can protect loaded drugs from experiencing sudden change in surrounding pH. The pH buffering capacity for HC is 1.1-3.0-fold higher than CS when various amounts of 0.1M HCl is added to the polymer.

The degree of hypromellose conjugation may be varied in order to tailor specific drug release profiles for a specific application. For example, the structure of HC may be modified with different functional components, including but not limited to photo-cross-linkable groups such as diacrylate and methacrylate groups, targeting ligands (such as transferrin and folic acid) and other polymers (e.g. polyethylene glycol (PEG)).

HC also loads drugs with very high efficiency (>90%), regardless of the size and water solubility of the drugs. For comparison, unmodified CS has a drug loading capacity around 50-60%. The drug encapsulation efficiency of HC is 1.1-3.0-fold higher than CS. HC also allows for highly sustained release of drugs, which in turn reduces the number of repeated drug administrations and eliminates the discomfort associated with periodic dosing, thereby improving patient compliance.

In addition, HC complexes with carboxymethyl cellulose (CMC) via electrostatic interactions. The ratio of HC to CMC may be adjusted for specific application scenarios. In some embodiments, the ratio of HC to CMC is 1:2, 1:3, 1:4, 1:5, 2:1, 2:3, 2:5, 3:1, 3:2, 3:4, 3:5, 4:1, 4:3, 4:5, 5:1, 5:2, 5:3, or 5:4. The polyelectrolyte complex formed by HC gives a drug encapsulation efficiency of over 90% in a few representative drugs tested, with a 1.5-5.0 fold longer duration of sustained drug release as compared to that formed by conventional CS. HC exhibits potential for drug delivery, in particular, for localized drug delivery to the skin, intestinal environment and other similar sites of interest. In one embodiment, the polyelectrolyte complex disclosed herein can be prepared simply by bulk mixing before use. This is highly user-friendly and convenient to clinical use, because prior technical training for the preparation of the formulation can be kept to a minimum.

In one embodiment, the polyelectrolyte complex disclosed herein is in the form of a gel. In one embodiment, the gel is prepared shortly prior to use. In one embodiment, the polyelectrolyte is in the form of a drug-loaded film. In one embodiment, the film is a stable long-term storage film. In one embodiment, the film is applied as a patch. In one embodiment, the polyelectrolyte complex is in the form of a dissolving film formulation. In certain embodiments, the film encapsulates hydrophilic and hydrophobic drugs. In certain embodiments, the film is administered orally.

Figure 1:
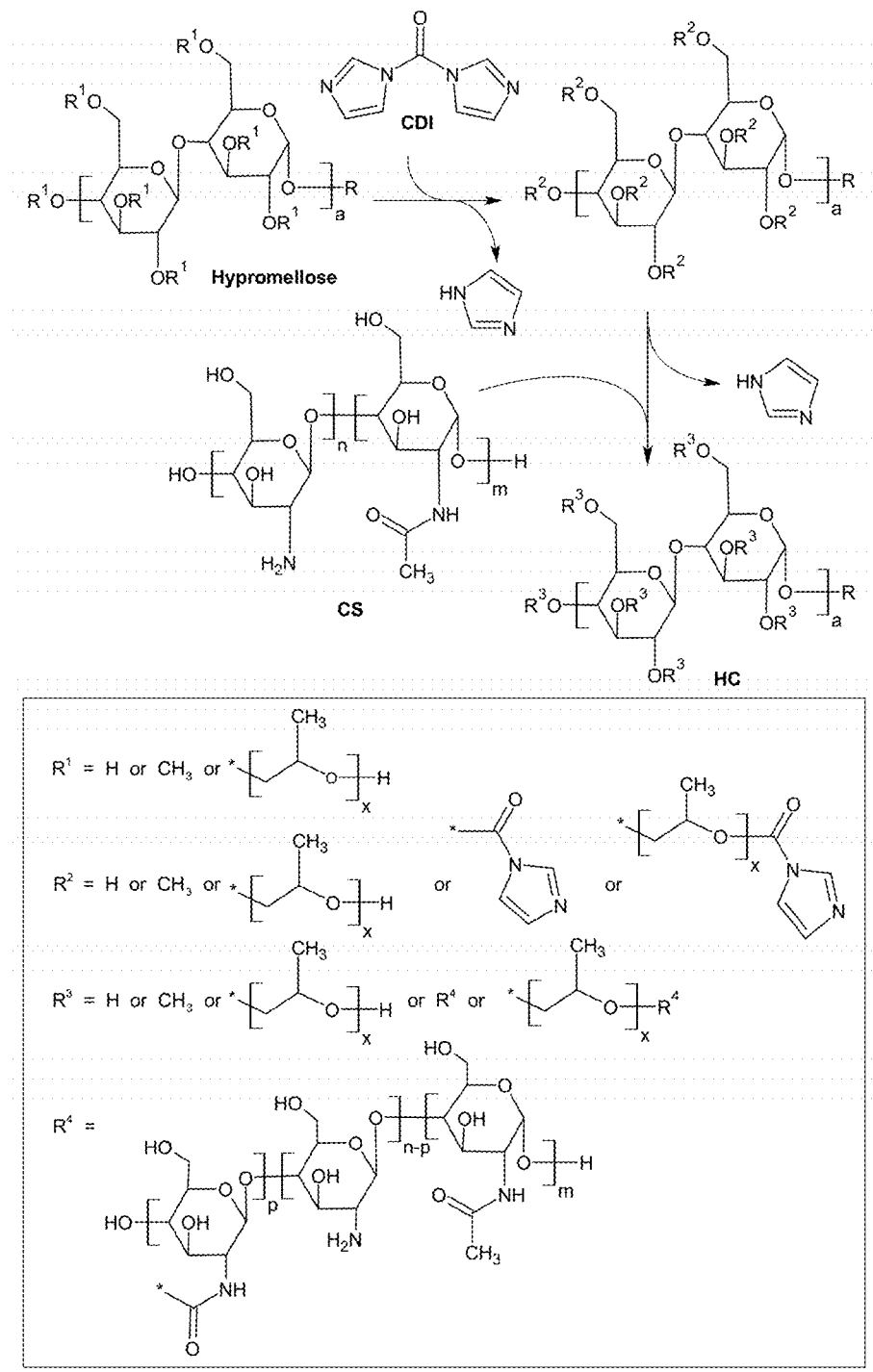

FIG. 1 depicts the synthesis of HC. During synthesis, hydroxyl groups of hypromellose molecules are activated by 1,1'-carbonyldiimidazole (CDI) to form active imidazolyl carbamate intermediates, which are then attacked by primary amine groups from CS, with imidazole being released as a by-product. Unreacted reactants are removed by dialysis against water.

Figure 2:
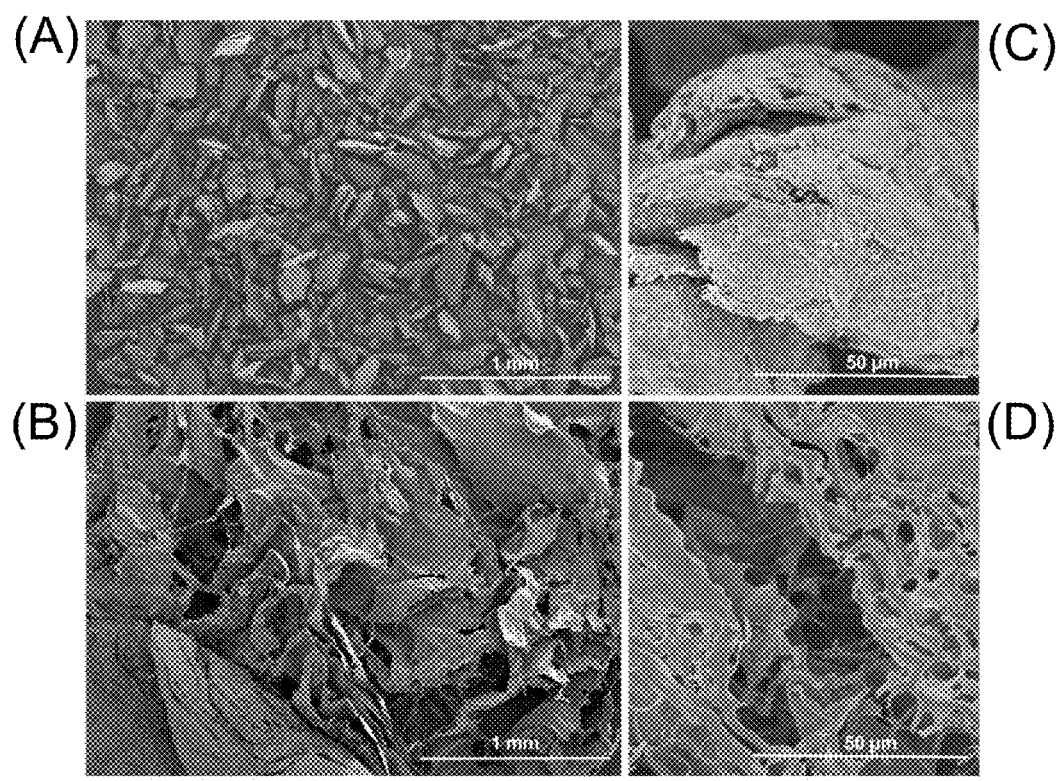

FIGS. 2(A) and (B) depict the surface morphologies of CS and HC by SEM. As shown in FIG. 2(A), conventional CS shows a granular surface morphology. In the case of HC as shown in FIG. 2(B), the granular morphology of CS is distorted due to the presence of grafted hypromellose chains, which agglomerated to transition the morphology of the graft copolymer to fibrillar. The fibrillar structure of HC facilitates the entrapment of drugs during drug loading.

Figure 3:
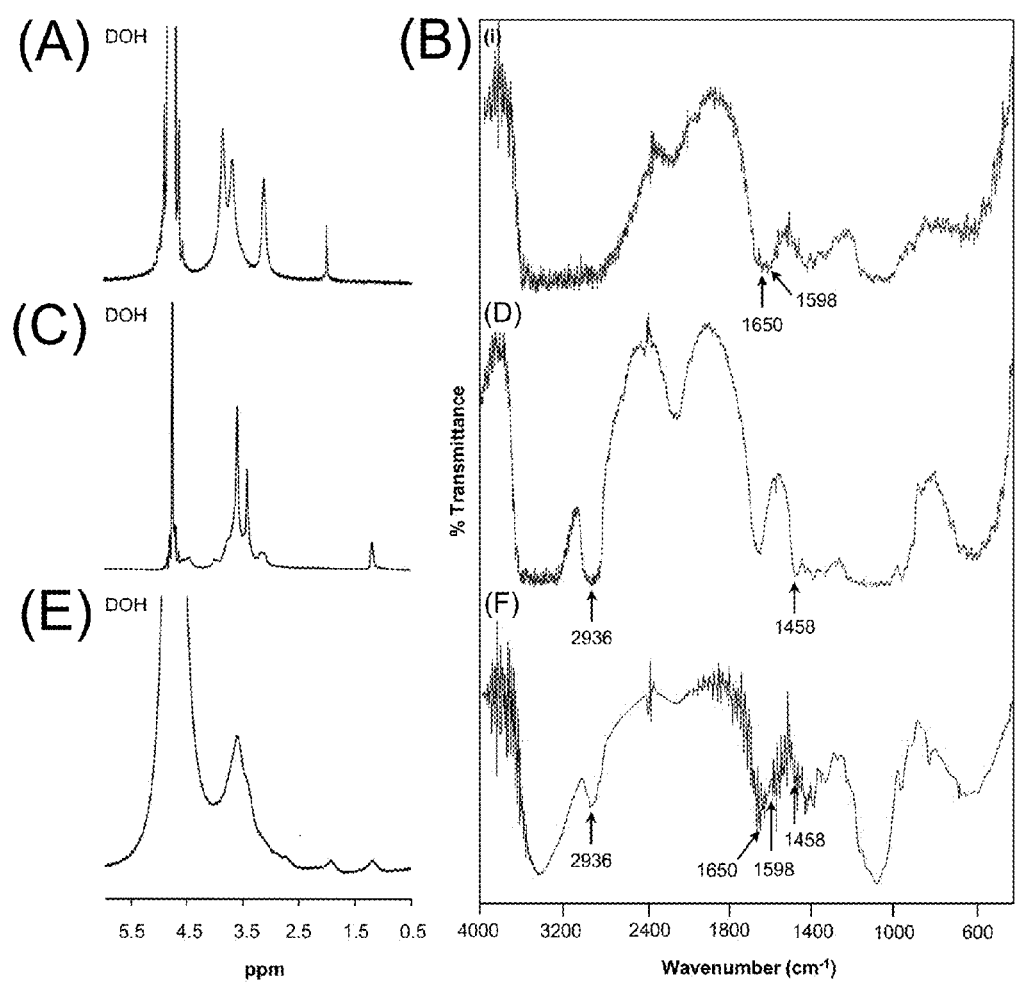

FIGS. 3(A) and (B) verify the success of CS/hypromellose graft copolymerization by $^1$H-NMR. A characteristic signal from CS at 1.97 ppm (NCOCH$_3$) is present in the spectrum of HC, in which the signal from hypromellose at 1.2 ppm, which is attributed to the methyl protons from the hydroxypropyl group, can be also observed. This suggests the successful grafting of hypromellose onto CS chain molecules.

FIG. 3(B) further depicts the structure of a successful grafting of hypromellose onto CS by Fourier transform infrared spectroscopy. The spectrum of hypromellose exhibits an absorption band at 2,936 cm$^{-1}$, which is assigned to C—H stretching of methyl and hydroxypropyl groups. A distinctive signal can also be observed at 1,458 cm$^{-1}$, which come from the asymmetric bending vibration of the methyl group in CH$_3$O. All these signals can be found in the spectrum of HC. On the other hand, distinctive absorption bands at 1,598 cm$^{-1}$ and 1,650 cm$^{-1}$ were detected in the spectra of HC and CS but not in the spectrum of hypromellose. These peaks are attributed to the N—H bending vibration (amide II) of a primary amino group and the carbonyl stretching vibration (amide I), respectively.

Figure 4:
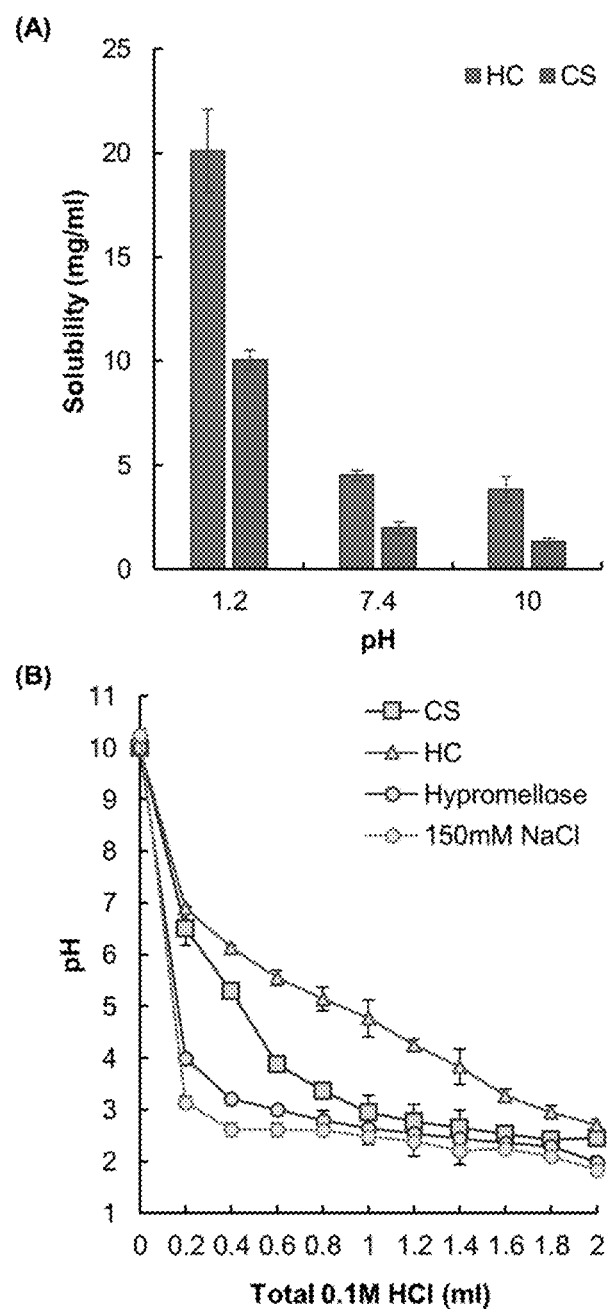

As hypromellose is a cellulose ether commonly used in the fabrication of hydrophilic matrices, incorporation of hypromellose to the hydrophobic CS molecules enhances the aqueous solubility of the resulting product. FIG. 4(A) shows the solubility of CS as compared to HC at different pH levels. The aqueous solubility of HC may vary with the degree of hypromellose coupling to CS. In specific embodiments, the aqueous solubility of HC is 2.01-, 2.26- and 2.95-fold higher than the aqueous solubility of conventional CS at pH values of 1.2, 7.4 and 10, respectively. The higher aqueous solubility of HC is attributable to the loss of some primary amine groups during copolymerization with hypromellose, and this weakens the intermolecular hydrogen bonds between CS molecules. The higher aqueous solubility of HC allows it to be dissolved in neutral solutions, and hence is more compatible with delivery of pH-sensitive drugs than conventional CS. In addition, due to the higher aqueous solubility of HC, formulation preparation can be done in an aqueous solution without the need for any organic solvents. This reduces some clinical issues with generating conventional CS capsules, which often require approaches using aqueous/organic systems.

FIG. 4(B) shows the pH buffering capacities of CS, hypromellose and HC via acid-base titration profiles. FIG. 4(B) demonstrates that HC has a higher buffering capacity than CS across a wide range of pH levels. HC's higher buffering capacity is due to the higher aqueous solubility of HC, which provides HC with a higher number of available amine groups in solutions to buffer changes in pH. The higher pH buffering capacity of HC can protect loaded drugs from drastic changes in pH (e.g. when the drug reaches the acidic conditions of the stomach) and can therefore provide a more pH-stable environment for drug encapsulation and drug delivery in practice.

Figure 5:
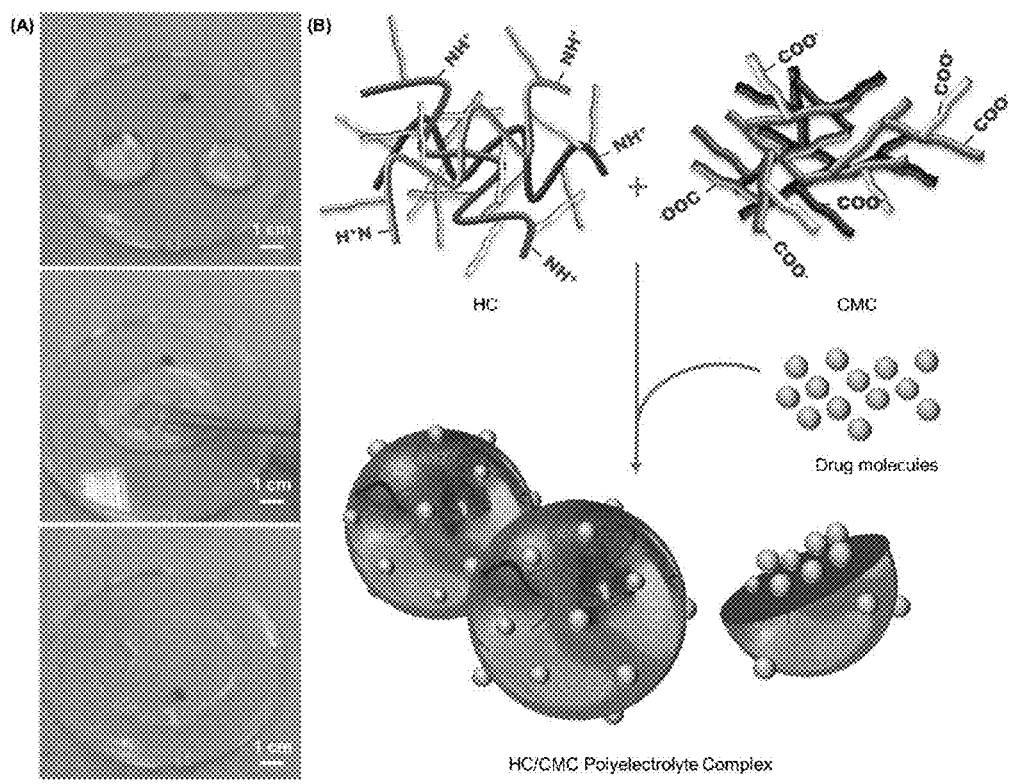

Current fabrication methods of CS-bared drug carriers typically take one of two approaches. One method uses CS directly for fabrication of capsules. However, this method requires CS to be dissolved in acidic media, which makes this method unfeasible for drugs that are highly pH-sensitive. This method sometimes requires organic solvents as well, which impose additional safety concerns for clinical applications. The second fabrication method is to complex CS with another polymer which is usually oppositely charged, for preparation of a hydrogel for controlled drug release. This approach is more flexible and is easier to prepare. Polyampholytic hydrogels are polymeric networks consisting of both positive and negative segments. Carboxymethyl cellulose (CMC) is one common polymer that may be complexed with CS or HC. FIGS. 5(A) and (B) show the preparation and complexation of an HC/CMC polyelectrolyte complex for encapsulation of a drug. The HC/CMC polyelectrolyte complex was prepared by mixing HC solution with an equal volume of CMC solution. The mixture was then left at ambient conditions for 10 minutes to give more time for gelation. The same approach was also used to prepare CS/CMC hydrogel, but the HC solution was replaced by acetic acid solution of CS. Compared to the polyelectrolyte complexes formed between CS and anionic polymers, those formed by HC achieve better drug encapsulation efficiency and more tunable drug release sustainability.

Figure 6:
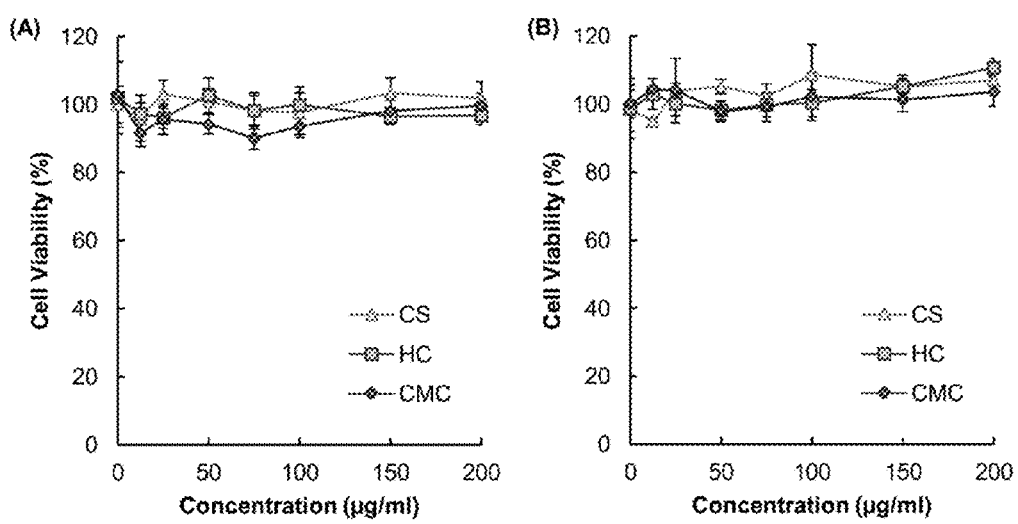

One of the factors in determining the practical potential of a drug delivery system is the toxicity of the system. FIGS. 6(A) and (B) show the toxicity of HC, CS and CMC in rat retinal Müller rMC-1 cells in an MTS assay after 5-hour and 24-hour incubations respectively. No significant toxicity of HC, CS and CMC has been observed in vitro in concentrations up to 200 μg/ml. This illustrates the high safety profile of HC and these polymers for biological use.

Provided herein as an exemplary embodiment is a HC/CMC formulation. The polyelectrolyte complexes are formed via electrostatic interactions by mixing the positively charged CS or HC molecules with the negatively charged CMC chains. CMC was selected in order to demonstrate the advantages of HC over conventional CS because of CMC's non-toxicity, non-allergenicity and biocompatibility. This is not intended to limit the disclosure to only formulations using CMC, as other suitable polymers may be blended with HC in order to achieve substantially similar drug delivery systems and methods.

Figure 7:
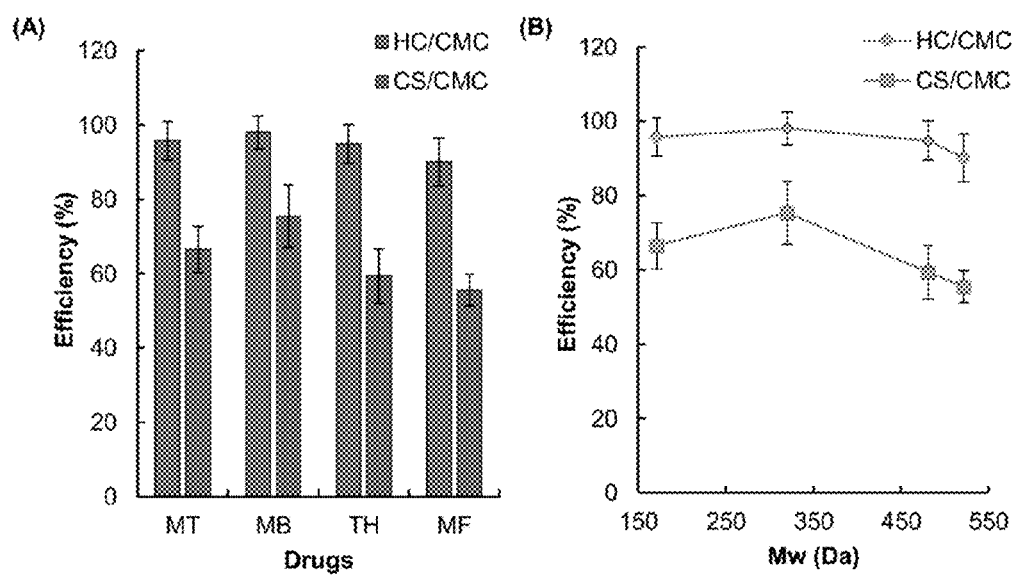

FIGS. 7(A) and (B) compare the drug encapsulation capacity and drug release sustainability of the CS/CMC polyelectrolyte complexes with those prepared by HC. Depending on the type of drug selected or the molecular weight, the drug encapsulation efficiency varies between 60-70% for CS/CMC and 90-95% for HC/CMC hydrogels. In some embodiments, the drug encapsulation efficiency of HC as compared to CS uses tetracycline chloride (TH), methylene blue (MB), mometasone furoate (MF) and metronidazole (MT), or any combination of drugs thereof. In other embodiments, other chemical drugs and even fragile drugs (such as nucleic acids, proteins and peptides) can also be adopted.

In some embodiments, the molecular weight of the drug selected ranges from 0-50, 51-100, 101-150, 151-200, 201-250, 251-300, 301-350, 351-400, 401-450, 451-500, 501-550, 550-600, 601-650, or 651-700 Da. In some embodiments, the drug encapsulation efficiency for HC is 75-80%, 80-85%, 85-90%, 90-92%, 92-94%, 94-96%, 96-98% or 98-100%. In some embodiments, the drug encapsulation efficiency for HC is 1.1-1.2 fold higher than the drug encapsulation efficiency for CS depending on the drug chosen. This disclosure provides for drugs of any molecular weight, but preferably provides for drugs between 0 Da and 600 Da, and more preferably for drugs between 100 Da and 500 Da. The lower encapsulation efficiency of CS reflects a greater drug loss during polyelectrolyte complexation. In the range of molecular weights examined, the effect of the size of the drug molecules on the encapsulation efficiency is not significant in both CS/CMC and HC/CMC hydrogels. The higher drug encapsulation capacity of HC/CMC is partially attributed to the alteration of CS upon graft copolymerization as shown in FIGS. 2(A) and (B). Due to the transition from the granular to fibrillar morphology upon hypromellose graft copolymerization, the fibrillar structure of HC increases the entrapment of molecules, including drugs, when the drug-loaded HC/CMC hydrogel is prepared.

Figure 8:
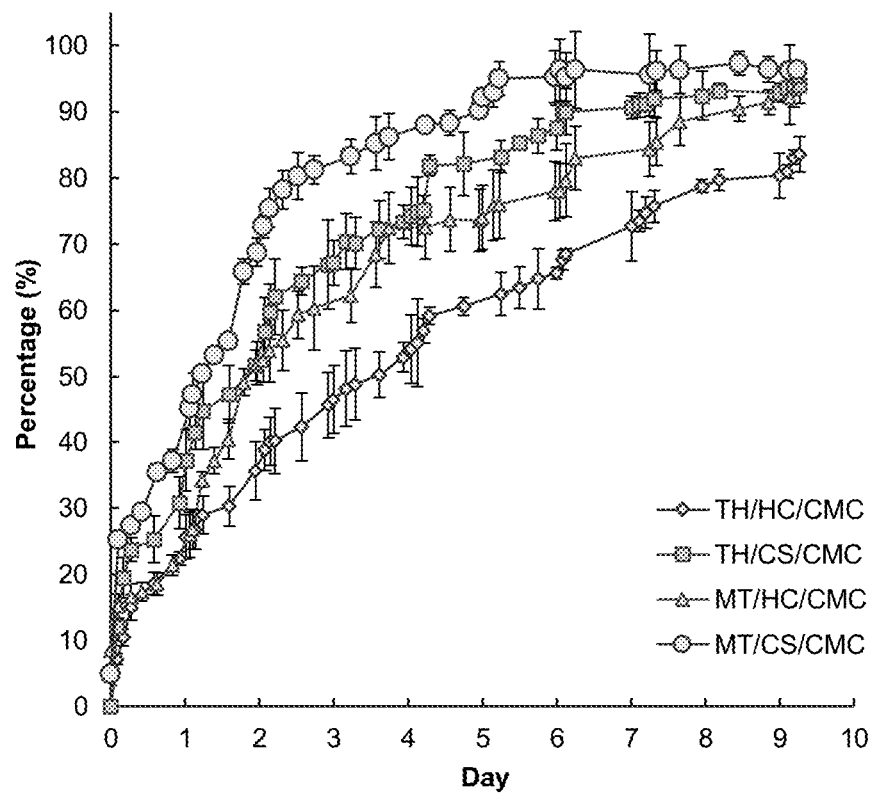
FIG. 8 is a graphical representation of the drug release profiles of HC/CMC and CS/CMC at 37° C.

While drug encapsulation capacity is important to development of drug carriers, the ability to limit drug release is also beneficial to maintain substantially constant therapeutic levels for prolonged periods and thereby reduce the total dose of administration. FIG. 8 shows the percentage of drug released at 37° C. for HC/CMC and CS/CMC hydrogels loaded with TH or MT. For either drug, the HC/CMC hydrogel shows improved drug release sustainability. In some embodiments, MT, MB, TH, MF, or any combination of drugs thereof are used to measure HC and CS drug release sustainability. In some embodiments, the drug release sustainability of complexes including HC are 1.5-1.6, 1.6-1.7, 1.7-1.8, 1.8-1.9, 1.9-2.0, 2.0-2.1, 2.1-2.2, 2.2-2.3, 2.3-2.4, 2.4-2.5, 2.5-2.6, 2.6-2.7, 2.7-2.8, 2.8-2.9, 2.9-3.0, 3.0-3.1 folds higher than complexes including CS. While CS/CMC leads to a release of approximately 80% of the encapsulated MT on day 3 and 80% of TH on day 4, HC/CMC counterparts release the same amount of drugs only on day 7 for MT and day 9 for TH.

Figure 9:
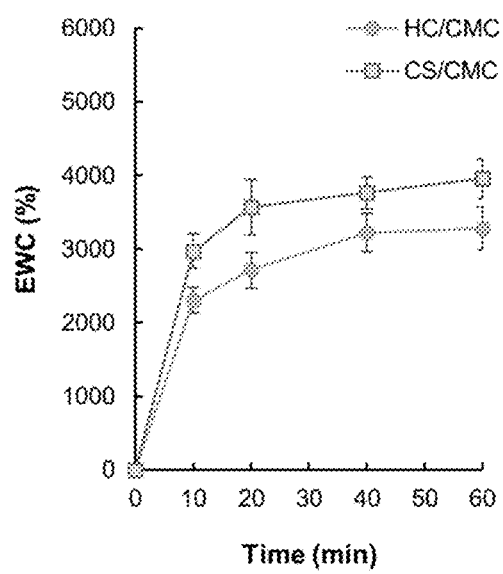
FIG. 9 is a graphical representation of the percentage change in equilibrium water content (EWC) as a function of time for HC/CMC and CS/CMC at the pH of 7.4.

The high drug release sustainability of HC/CMC is attributed to copolymerization of CS with hypromellose, which leads to cross-linking among CS molecules. Such cross-linking restricts the mobility of CMC chains in the polyelectrolyte complex, thereby reducing the swelling capacity of the complex formed between CMC and HC. The swelling capacity of the complex affects the release profile because water in the matrix is the medium through which the drug will diffuse. As both the swelling and equilibrium water content (EWC) of a hydrogel depend largely on the amount of water the hydrogel can take up upon hydration, they are closely related to each other and demonstrate similar trends. Therefore, the EWC of a hydrogel has been widely used as an indicator of the swelling property. FIG. 9 shows the lower EWC of the HC/CMC complex compared to the CS/CMC complex, and therefore indicates a lower swelling capacity. In some embodiments the swelling property of the HC complex is proportional to the EWC of the HC complex. In some embodiments, the swelling property of the HC complex is 1.5-1.6, 1.6-1.7, 1.7-1.8, 1.8-1.9, 1.9-2.0, 2.0-2.1, 2.1-2.2, 2.2-2.3, 2.3-2.4, 2.4-2.5, 2.5-2.6, 2.6-2.7, 2.7-2.8, 2.8-2.9, 2.9-3.0, 3.0-3.1, 3.1-3.2, 3.2-3.3, 3.3-3.4, 3.4-3.5, 3.5-3.6, 3.6-3.7, 3.7-3.8, 3.8-3.9, 3.9-4.0, 4.0-4.1, 4.1-4.2, 4.2-4.3, 4.3-4.4, 4.4-4.5, 4.5-4.6, 4.6-4.7, 4.7-4.8, 4.8-4.9, or 4.9-5.0 fold lower than the swelling property of the CS complex. Apart from cross-linking, the number of available amine groups from CS have been reduced after graft copolymerization. The osmotic pressure built up inside the complex can therefore be reduced because of the discounted ability of HC as compared to CS to form hydrogen bonds between HC and water molecules. This may further lower the swelling of the HC/CMC polyelectrolyte complex, thereby lowering the release rate of the encapsulated drugs. In some embodiments, the release rate of the encapsulated drugs for the HC complex is 1.1-1.2, 1.2-1.3, 1.3-1.4, 1.4-1.5, 1.5-1.6, 1.6-1.7, 1.7-1.8, 1.8-1.9, 1.9-2.0, 2.0-2.1, 2.1-2.2, 2.2-2.3, 2.3-2.4, 2.4-2.5, 2.5-2.6, 2.6-2.7, 2.7-2.8, 2.8-2.9, or 2.9-3.0 fold lower than the CS complex.

MODE OF ADMINISTRATION

The present compositions, which comprise a matrix and a drug, are administered by infusion or bolus injection, by absorption through epithelial or mucocutaneous linings (e.g., oral mucosa, rectal and intestinal mucosa, etc.) or orally and may be administered together with another biologically active agent. Administration can be systemic or local. Various delivery systems are known. In certain embodiments, the composition is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the drug into the bloodstream.

In specific embodiments, it may be desirable to administer the composition locally to the area in need of treatment or prevention of a disorder. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including films or membranes, such as sialastic membranes, or fibers. In one embodiment, administration can be by direct injection at the site (or former site).

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds can be formulated as a suppository, with traditional binders and vehicles such as triglycerides.

In yet another embodiment, the composition can be delivered in an additional controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, an additional polymeric materials can be used as a carrier (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). The use of a efficient controlled-release system will require only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533).

DOSAGE

The amount of a composition that will be effective in the treatment or prophylactic use of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In specific preferred embodiments of the invention, the oral dose is 0.01 milligram to 70 milligrams per kilogram body weight, more preferably 0.1 milligram to 50 milligrams per kilogram body weight, more preferably 0.5 milligram to 20 milligrams per kilogram body weight, and yet more preferably 1 milligram to 10 milligrams per kilogram body weight. In a most preferred embodiment, the oral dose is 5 milligrams of drug per kilogram body weight. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of drug per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the drug for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

REFERENCES

Oh J E, Nam Y S, Lee K H, Park T G. Conjugation of drug to poly(D,L-lactic-co-glycolic acid) for controlled release from biodegradable microspheres. Journal of Controlled Release. 1999; 57:269-80.

Nam Y S, Park J Y, Han S H, Chang I S. Intracellular drug delivery using poly(D,L-lactide-co-glycolide) nanoparticles derivatized with a peptide from a transcriptional activator protein of HIV-1. Biotechnology Letters. 2002; 24:2093-8.

Luo R C, Cao Y, Shi P, Chen C H. Near-infrared light responsive multi-compartmental hydrogel particles synthesized through droplets assembly induced by superhydrophobic surface. Small. 2014; 10:4886-94.

Kearns V R, Williams R L. Drug delivery systems for the eye. Expert Review of Medical Devices. 2009; 6:277-90.

Chu L Y, Yamaguchi T, Nakao S. A molecular-recognition microcapsule for environmental stimuli-responsive controlled release. Advanced Materials. 2002; 14:386-9.

Kim S H, Kim J W, Kim D H, Han S H, Weitz D A. Polymersomes containing a hydrogel network for high stability and controlled release. Small. 2013; 9:124-31.

Kolhe P, Misra E, Kannan R M, Kannan S, Lieh-Lai M. Drug complexation, in vitro release and cellular entry of dendrimers and hyperbranched polymers. International Journal of Pharmaceutics. 2003; 259:143-60.

Feng X L, Lv F T, Liu L B, Tang H W, Xing C F, Yang Q O, et al. Conjugated polymer nanoparticles for drug delivery and imaging. ACS Applied Materials & Interfaces. 2010; 2:2429-35.

Xu X D, Liang L A, Chen C S, Lu B, Wang N L, Jiang F G, et al. Peptide hydrogel as an intraocular drug delivery system for inhibition of postoperative scarring formation. ACS Applied Materials & Interfaces. 2010; 2:2663-71.

Manna U, Patil S. Glucose-triggered drug delivery from borate mediated layer-by-layer self-assembly. ACS Applied Materials & Interfaces. 2010; 2:1521-7.

Fatouros D G, Lamprou D A, Urquhart A J, Yannopoulos S N, Vizirianakis I S, Zhang S G, et al. Lipid-like self-assembling peptide nanovesicles for drug delivery. ACS Applied Materials & Interfaces. 2014; 6:8184-9.

Zhao J, Lu C, He X, Zhang X, Zhang W, Zhang X. Polyethylenimine-grafted cellulose nanofibril aerogels as versatile vehicles for drug delivery. ACS Applied Materials & Interfaces. 2015; 7:2607-15.

Lima H A, Lia F M V, Ramdayal S. Preparation and characterization of chitosan-insulin-tripolyphosphate membrane for controlled drug release: effect of cross linking agent. Journal of Biomaterials and Nanobiotechnology. 2014; 5:211-9.

Oral drugs comprising absorbent-containing granules and cathartics, and their manufacture. 2010. JP 2010235537A Li C L, Martini L G, Ford J L, Roberts M. The use of hypromellose in oral drug delivery. Journal of Pharmacy and Pharmacology. 2005; 57:533-46.

A sustained release pharmaceutical formulation. 2002. WO2014197601A1

Nunthanid J, Huanbutta K, Luangtana-Anan M, Sriamornsak P, Limmatvapirat S, Puttipipatkhachorn S. Development of time-, pH-, and enzyme-controlled colonic drug delivery using spray-dried chitosan acetate and hydroxypropyl methylcellulose. European Journal of Pharmaceutics and Biopharmaceutics. 2008; 68:253-9.

Kim S K, Rajapakse N. Enzymatic production and biological activities of chitosan oligosaccharides (COS): A review. Carbohydrate Polymers. 2005; 62:357-68.

Pal S, Nasim T, Patra A, Ghosh S, Panda A B. Microwave assisted synthesis of polyacrylamide grafted dextrin (Dxt-g-PAM): Development and application of a novel polymeric flocculant. International Journal of Biological Macromolecules. 2010; 47:623-31.

Shahid M, Bukhari S A, Gul Y, Munir H, Anjum F, Zuber M, et al. Graft polymerization of guar gum with acryl amide irradiated by microwaves for colonic drug delivery. International Journal of Biological Macromolecules. 2013; 62:172-9.

Lorenzo-Lamosa M L, Remunan-Lopez C, Vila-Jato J L, Alonso M J. Design of microencapsulated chitosan microspheres for colonic drug delivery. Journal of Controlled Release. 1998; 52:109-18.

Nakagawa K, Sowasod N, Tanthapanichakoon W, Charinpanitkul T. Hydrogel based oil encapsulation for controlled release of curcumin by using a ternary system of chitosan, kappa-carrageenan, and carboxymethylcellulose sodium salt. LWT-Food Science and Technology. 2013; 54:600-5.

Lu S Y, Liu M Z, Ni B L. An injectable oxidized carboxymethylcellulose/N-succinyl-chitosan hydrogel system for protein delivery. Chemical Engineering Journal. 2010; 160:779-87.

Gomez-Burgaz M, Garcia-Ochoa B, Torrado-Santiago S. Chitosan-carboxymethylcellulose interpolymer complexes for gastric-specific delivery of clarithromycin. International Journal of Pharmaceutics. 2008; 359:135-43.

Yan L F, Qian F, Zhu Q S. Interpolymer complex polyampholytic hydrogel of chitosan and carboxymethyl cellulose (CMC): synthesis and ion effect. Polymer International. 2001; 50:1370-4.

Alencastre J B, Bentley M V L B, Garcia F S, de Moragas M, Viladot J L, Marchetti J M. A study of the characteristics and in vitro permeation properties of CMC/chitosan microparticles as a skin delivery system for vitamin E. Revista Brasileira de Ciências Farmacêuticas. 2006; 42:69-76.

Li P, Dai Y N, Zhang J P, Wang A Q, Wei Q. Chitosan-alginate nanoparticles as a novel drug delivery system for nifedipine. International Journal of Biomedical Science. 2008; 4:221-8.

Mellott M B, Searcy K, Pishko M V. Release of protein from highly cross-linked hydrogels of poly(ethylene glycol) diacrylate fabricated by UV polymerization. Biomaterials. 2001; 22:929-41.

Lee J W, Kim S Y, Kim S S, Lee Y M, Lee K H, Kim S J. Synthesis and characteristics of interpenetrating polymer network hydrogel composed of chitosan and poly(acrylic acid). Journal of Applied Polymer Science. 1999; 73:113-20.

Lai and Shum. Hypromellose-graft-chitosan and its polyelectrolyte complex as novel systems for sustained drug delivery. ACS Appl Mater Interfaces. 2015: 7(19):10501-10.

What is claimed is:

1. A drug delivery system for controlled and sustained delivery of an effective amount of a drug to a subject, comprising:
   a matrix comprising: (i) a hypromellose-graft-chitosan (HC); or (ii) a HC polyelectrolyte complex; and
   one or more drugs dispersed in the matrix.

2. The drug delivery system according to claim 1, wherein the drug is: tetracycline chloride (TH), methylene blue (MB), mometasone furoate (MF), metronidazole (MT), or a combination thereof.

3. The drug delivery system according to claim 1, wherein the drug is delivered via localized drug delivery.

4. The drug delivery system according to claim 1, which is a medical device, a wound dressing, a gel, a patch, a film, a bandage, a tablet, a pill, or a paste.

5. The drug delivery system according to claim 4 which is a film.

6. The drug delivery system of claim 1 wherein the HC is further modified by photo-cross-linkable groups including diacrylate groups, methacrylate groups, targeting ligands, and polymers.

7. A method for delivering drugs to a subject comprising the step of administering to said subject the drug delivery system according to claim 1.

8. A method of claim 7, wherein the drug is delivered via implantation, topical delivery, or ingestion of the drug delivery system.

9. The method of claim 7, wherein the drug delivery system is a wound dressing, gel, patch, film, bandage, tablet, pill, or paste.

10. The method of claim 9 wherein the drug delivery system is a film.

11. The method of claim 7 wherein the drug is delivered via localized drug delivery.

12. A method of preparing a drug delivery system comprising the steps of:

reacting chitosan with hypromellose to form a matrix comprising hypromellose-graft-chitosan (HC); and dispersing a drug in the matrix.

13. The method of claim 12 further comprising the step of reacting the HC with a polyelectrolyte to form a HC polyelectrolyte complex prior to dispersing the drug in the matrix.

14. The method according to claim 12, wherein the HC is formed by reacting hypromellose and chitosan in the presence of 1,1'-carbonyldiimidazole (CDI).

15. The method according to claim 13, wherein the polyelectrolyte is carboxymethyl cellulose (CMC).

16. The method according to claim 12, wherein the delivery system is a wound dressing, gel, patch, film, bandage, tablet, pill, or paste.

17. The method according to claim 16 wherein the delivery system is a film.

18. The method according to claim 12 wherein the HC is further modified by diacrylate, methacrylate, targeting ligands, and polymers.

19. The drug delivery system of claim 6 wherein the targeting ligands are transferrin and folic acid and the polymers are polyethylene glycol.

20. A polymer for drug delivery comprising a hypromellose-graft-chitosan (HC) wherein the HC is formed by reacting hypromellose with chitosan.

21. A polymer for drug delivery comprising a HC polyelectrolyte complex which is formed by reacting a HC with a polyelectrolyte.

22. The polymer of claim 21 wherein the polyelectrolyte is carboxymethyl cellulose (CMC).

* * * * *